(12) United States Patent
Li et al.

(10) Patent No.: US 11,632,970 B2
(45) Date of Patent: Apr. 25, 2023

(54) VITAMIN AND CAROTENOID POWDER AND ITS PREPARATION METHOD AND APPLICATION

(71) Applicants: ZHEJIANG NHU COMPANY LTD., Shaoxing (CN); ZHEJIANG UNIVERSITY, Hangzhou (CN)

(72) Inventors: Jiandong Li, Shaoxing (CN); Zhirong Chen, Hangzhou (CN); Hong Yin, Hangzhou (CN); Xiaoyong Zhu, Shaoxing (CN); Dan Qiu, Ningbo (CN); Lifang Shi, Shaoxing (CN); Dongming Shi, Shaoxing (CN); Yong Qi, Shaoxing (CN)

(73) Assignees: ZHEJIANG NHU COMPANY LTD., Shaoxing (CN); ZHEJIANG UNIVERSITY, Hangzhou (CN)

( * ) Notice: Subject to any disclaimer, the term of this patent is extended or adjusted under 35 U.S.C. 154(b) by 1320 days.

(21) Appl. No.: 16/067,528

(22) PCT Filed: Dec. 8, 2016

(86) PCT No.: PCT/CN2016/108968
§ 371 (c)(1),
(2) Date: Jun. 29, 2018

(87) PCT Pub. No.: WO2017/114120
PCT Pub. Date: Jul. 6, 2017

(65) Prior Publication Data
US 2021/0161175 A1     Jun. 3, 2021

(30) Foreign Application Priority Data

Dec. 31, 2015 (CN) .......................... 201511030503.4

(51) Int. Cl.
| | | |
|---|---|---|
| *A23K 20/174* | (2016.01) | |
| *A23K 40/30* | (2016.01) | |
| *A23P 10/30* | (2016.01) | |
| *A23L 33/15* | (2016.01) | |
| *A61K 9/14* | (2006.01) | |
| *A61K 31/015* | (2006.01) | |

(52) U.S. Cl.
CPC ............ *A23K 20/174* (2016.05); *A23K 40/30* (2016.05); *A23L 33/15* (2016.08); *A23P 10/30* (2016.08); *A61K 9/146* (2013.01); *A61K 31/015* (2013.01)

(58) Field of Classification Search
CPC ....... A23K 20/174; A23K 40/30; A23P 10/30; A23L 33/15; A61K 9/146; A61K 2300/00; A62K 31/015
See application file for complete search history.

(56) References Cited

U.S. PATENT DOCUMENTS

| | | | | |
|---|---|---|---|---|
| 3,565,559 A | * | 2/1971 | Ryota et al. ......... | A61K 9/5089 424/492 |
| 5,229,147 A | * | 7/1993 | Kubota ................. | A23K 40/30 426/805 |
| 6,391,288 B1 | * | 5/2002 | Miyazawa .......... | A61K 9/5036 424/463 |

FOREIGN PATENT DOCUMENTS

| | | |
|---|---|---|
| CN | 104274428 | 1/2015 |
| CN | 104855548 | 8/2015 |

* cited by examiner

*Primary Examiner* — Hong T Yoo
(74) *Attorney, Agent, or Firm* — Jiwen Chen; Joywin IP Law PLLC

(57) ABSTRACT

The present invention discloses a method for preparation of vitamin and carotenoid powder; the vitamin and carotenoid powder comprises vitamin, carotenoid microcapsule and physical gel protection film covered on the surface of the vitamin and carotenoid microcapsule; the physical gel protection film is made from super-molecular system; the super-molecular system comprises the following constituents of parts in weight: vegetable oil: 6-30 parts; gel: 0.5-3 parts and antioxidant: 0.5-3 parts. The hot super-molecular solution is sprayed on the surface of cold vitamin and carotenoid microcapsule during preparation to form a specific 3D network structure that is used to bind the liquefied vegetable oil to form a physical gel protection film; the physical gel protection film has improved product storage stability as well as the its stability for application in feedstuff, food and health care products.

14 Claims, No Drawings ized application of PCT Application No. PCT/CN2016/108968 under 35 U.S.C. 371, filed Dec. 8, 2016 in Chinese, claiming priority of Chinese Application No. 201511030503.4, filed Dec. 31, 2015, all of which are hereby incorporated by reference

VITAMIN AND CAROTENOID POWDER AND ITS PREPARATION METHOD AND APPLICATION

This is a U.S. national stage application of PCT Application No. PCT/CN2016/108968 under 35 U.S.C. 371, filed Dec. 8, 2016 in Chinese, claiming priority of Chinese Application No. 201511030503.4, filed Dec. 31, 2015, all of which are hereby incorporated by reference

FIELD OF THE INVENTION

The present invention is related to a preparation method for improvement of stability of vitamin and carotenoid powder, which falls into the field of integrating production technique of feeder/food ingredients with super-molecular chemical technology.

BACKGROUND TECHNOLOGY

Super-molecular chemistry is a science established in recent years, which aims to study the super-molecular system with specific structure and functions as formed through inter-molecular interaction among more than two chemical species. It has witnessed an accelerated development and extensive application in sciences of materials, information and life. In particularly, following gelation, vegetable oil can form a thermally reversible physical gel with high resistance to oil migration. The gel will dissolve during heating, which may form a fiber structure through such inter-molecular interactions as hydrogen bond, coordination, Van Der Waals Force, static electricity and π-π stacking. Such fiber structures are further wound to form a 3D network, or form an inverted helical tubular structure through self-assembly. It may also form gel plastic fat through changing interfacial tension to make liquefied oil molecule to lose fluidity. The gel plastic fat has the advantages of quick crystallization and high resistance to oil migration, which is a remarkable soft material at present. It can be extensively applied to such fields as feeder, food and health care products.

Vitamin is a kind of micro organic regulating substance that is to be obtained from food by human beings and animals to maintain normal physiological functions. It plays an important role in the process of body growth, metabolism and development. Carotenoid is a general term of important natural pigments, which can improve fecundity and immune functions of animals. It has numerous physiological functions, such as anti-oxidation, pigmentation and enhancement of interlink between cell and cell gap. Carotenoid is to be externally supplemented from food or feeder as it is unavailable for synthesis in the body, or the quantity of synthesis is inadequate.

Vitamin and carotenoid belong to extremely instable substances that are extremely sensitive to light, heat and oxygen, which is inappropriate for addition into the feedstuff or food. Therefore, many researchers and companies have developed their own methods for stabilizing these active substances. For instance, CN 103315370 A aims to prepare a relatively stable carotenoid powder by dissolving carotenoid in the organic solvent, and adding it into the aqueous phase made from protective gel under high-speed shear prior to removal of solvent through heating, spraying and drying. WO2005/013708 discloses a fat-soluble vitamin and carotenoid powder made from milk protein, carbonhydrate and reduced sugar subjecting to crosslink and covering by crosslink agent. The vitamin and carotenoid contained in it include vitamins, carotenoids, polyunsaturated fatty acids and so on. U.S. Pat. No. 6,328,995 introduces a stable vitamin and/or carotenoid microcapsule and its production method. According to this method, one or more 0.1%~20% fat-soluble vitamins and/or one or more carotenoids are dispersed into a mixture containing 2%~40% of protein, 1%~30% of at least one sugar, 0.2%~20% $K_2HPO_4$ and $Na_2HPO_4$; other constituents are prepared through spraying and drying in the water system. What mentioned above are powder products with respective advantages, which can improve stability of active substance to some extent. However, they also have common disadvantages: (1) there are gaps and pores on the powder wall more or less, and oxygen coming in from such gaps and pores will contact with vitamin and carotenoid to reduce its content; (2) covering of microcapsule products may more or less produce residual core materials on its surface, which may inevitably and directly result in loss of partial vitamin and carotenoid. If it is added into the premix, such active constituents as astaxanthin are to be reduced by 35%~48% due to the impact from processing of feedstuff [Ind. Aliment. Agric. (1987) 104:529-533; Aquaculture Ind. Develop. Report (1991) 91:34-51]. When vitamin A acetate powder is used to milk powder to prepare fortified nutritive milk powder for infants, its content may reduce by 18%~25% after storage of the milk powder for 6 months under the temperature of 40° C. and humidity of 75%. When lycopene powder is used to health care products, and prepared into tablets through compressing, its content may reduce by 20%~32% after storage for 6 months under the temperature of 40° C. and humidity of 75%. With regard to canthaxanthin powder used to feedstuff, its content will reduce by 15%~27% when the feedstuff is accelerated for 1 month under the temperature of 60° C. and humidity of 75%. Stability of partial powder preparation can be further improved during storage, and its application stability in feed, food and health care products also has much room for improvement.

In view of aforesaid disadvantages, researchers dissolve some active fat-soluble substances in the high-temperature oil phase to prepare oil suspension preparations so as to effectively prevent loss of active substances during processing of feedstuff under high temperature and pressure. For instance, WO2011/145659 discloses a method for preparation of a compound containing carotenoid. According to this method, oil-phase intermixture is to be heated under the temperature above the melting point of carotenoid to obtain oil-phase compound containing carotenoid. U.S. Pat. No. 8,748,495 introduces a carotenoid oil suspension of low viscosity and high fluidity; the carotenoid crystal added into the oil suspension is prepared through a series of processing, such as heating and mixing. As disclosed by CN 101396068 A, carotenoid is mixed with edible fat to prepare oil powder solution of small particle size through grinding, heating and mixing, which has improved stability of carotenoid to some extent. However, application of oil suspension solution in feedstuff, food and health care products is not convenient as that of powder, which has restricted its application in large scale.

SUMMARY OF THE INVENTION

In view of disadvantages and defects to vitamin and carotenoid of prior art, present invention provides a vitamin and carotenoid powder as well as its preparation method. Such vitamin and carotenoid powder has higher stability and are convenient for use.

A vitamin and carotenoid powder, comprising a vitamin and carotenoid microcapsule and a physical gel protection film surrounding entire surface of the vitamin and carotenoid microcapsule;

The physical gel protection film is made from a super-molecular system; the super-molecular system comprises the following constituents of parts by weight:

| | |
|---|---|
| Vegetable oil | 6~30 parts, |
| Gel | 0.5~3 parts, and |
| Antioxidant | 0.5~3 parts. |

The present invention makes use of super-molecular chemical technology to adjust interaction among constituents of the super-molecular system by starting from a submicroscopic structure for the purpose of adjustment and change of macroscopic physiochemical properties of the system. More specifically, it aims to produce a physical gel protection film formed by super-molecular system on the surface of vitamin and carotenoid microcapsule to prevent oxidation of active constituents by the air flowing into the vitamin and carotenoid microcapsule. On the other hand, it has high resistance to oil migration, which can prevent overflow of active constituents, and effectively improve its stability.

In the present invention, the vitamin and carotenoid powder refers to the powder independently taking vitamin or carotenoid as active constituent, or the powder containing both vitamin and carotenoid that serve as active constituent.

Wherein, the process for formation of the physical gel protection film is stated as follows:

Making vitamin and carotenoid microcapsule thoroughly suspend in the fluidizing air through ventilation; after that, spraying the super-molecular system on the surface of vitamin and carotenoid microcapsule when it is hot to form the physical gel protection film.

In a preferred embodiment, the vegetable oil is one of soybean oil, rap oil, maize oil, sunflower seed oil, peanut oil and salad oil at least. In a preferred embodiment, the gel is one of rice bran wax, carnauba wax, bee wax, candelilla wax and glycerol monostearate or mixture of γ-oryzanol and β-rhamno.

In a further preferred embodiment, the antioxidant is one of tocopheryl, ethoxyquin, BHT and TBHO at least.

In a further preferred embodiment, content of the vitamin and carotenoid microcapsule in the powder is 64%-93%.

In a further preferred embodiment, the vitamin and carotenoid microcapsule comprises the following compositions of parts by weight:

| | |
|---|---|
| Vitamin and carotenoid | 10.9-36.5 parts, |
| Antioxidant A | 0.1-1 part, and |
| Water soluble colloid | Supplemented to 100 parts. |

In a further preferred embodiment, the antioxidant A is vitamin C, vitamin C sodium salt, iso-vitamin C or iso-vitamin C sodium salt;

The water soluble colloid is starch octenyl succinate, gelatin or acacia.

In a further preferred embodiment, the vitamin and carotenoid are at least one of vitamin A palmitate, vitamin A acetate, vitamin D3, vitamin E acetate, vitamin K1, β-carotene, astaxanthin, lycopene, canthaxanthin and lutein.

Wherein, vitamin and carotenoid microcapsule can be obtained with existing method in this field. In a preferred embodiment, it is prepared through spraying and drying by taking gelatin, acacia or starch octenyl succinate as the wall material and vitamin and carotenoid as core material.

In the present invention, as a simple and effective method for formation of physical gel protection film, the hot super-molecular system is sprayed on the suspending vitamin and carotenoid microcapsule.

The present invention further provides a method for preparation of the vitamin and carotenoid powder, comprising the following steps:

(1) Dissolving the gel and antioxidant in the hot vegetable oil evenly to form a super-molecular solution;

(2) Making vitamin and carotenoid microcapsule thoroughly suspend in the fluidizing air through ventilation;

(3) Spraying the super-molecular solution as obtained in Step (1) on the surface of vitamin and carotenoid microcapsule when it is hot to form a physical gel protection film, and eventually obtain the vitamin and carotenoid powder.

According to this preparation method, all constituents of super-molecular system are to be preliminarily cooled for gelation during contact with microcapsule. It may produce a 3D network structure covered on the surface of microcapsule through self-assembly, and thereby form a physical gel protection film to effectively prevent ingression of oxygen and overflow of active constituents, improve its stability.

In a preferred embodiment, temperature of fluidized air in Step (2) is 0~30° C.;

In Step (3), temperature of super-molecular solution as sprayed is 70~100° C.

The present invention also provides a food, comprising the vitamin and carotenoid powder that serves as an additive. It is applicable to prepare enriched nutritive food through addition of the vitamin and carotenoid powder; for instance, it is applicable to obtain enriched nutritive four by adding the vitamin and carotenoid powder into common flour. Furthermore, it is applicable to obtain enriched nutritive milk powder by adding the vitamin and carotenoid powder into common milk powder.

The present invention further provides a health care product, comprising the vitamin and carotenoid powder as well as accessories. For instance, it is applicable to use the vitamin and carotenoid powder as well as appropriate accessories to prepare tablets for use.

The present invention further provides a feedstuff, comprising the vitamin and carotenoid powder that serves as an additive. It is applicable to obtain more nutritive feedstuff by adding the vitamin and carotenoid powder of the patent application and other nutritional ingredient into common feedstuff (such as rice chaff).

As compared with prior arts, the present invention has the following beneficial effect:

(1) The 3D network structure or inverted helical tubular structure formed by constituents of the super-molecular system through crystallization or self-assembly during cooling will be further wound to form a gel fat film. Such fat film is covered on the surface of the microcapsule, which can effectively block gaps and pores on the surface of microcapsule to prevent contact and reaction between oxygen coming in from pore and the vitamin as well as carotenoid, and thereby significantly improve storage and application stability of the vitamin and carotenoid.

(2) Gel fat film has high resistance to oil migration, which can effectively prevent outward migration of vitamin and carotenoid through the fat film; furthermore, it can maintain vitamin and carotenoid as contained in the powder to the maximum, minimize the loss of vitamin and carotenoid, and improve its stability.

DETAILED DESCRIPTION OF THE PREFERRED EMBODIMENTS

Comparative Example 1

816.0 g of modified starch by weighing was provided, and it was thoroughly dissolved through being mixed in 1.2 L water that was pre-heated to the temperature of 80° C. for further use as a wall material solution. 155.2 g retinol palmitate crystal and 6.3 g BHT (2,6-di-tert-butyl-4-methylphenol) were weighed, and dissolved in 147.1 g maize oil heated to the temperature of 60° C. When it was still hot, the aforesaid wall material solution was added into it to prepare an emulsified solution through high-speed shearing. The aforesaid emulsified solution was made into 954.5 g retinol palmitate microcapsules through spraying and drying. Initial content of retinol palmitate in the microcapsule was measured. 500.0 g aforesaid microcapsule by weighing was provided, and packed into the aluminum foil bag for acceleration for 6 months under the temperature of 40° C.±2° C. and humidity of 75%±5%. The content of retinol palmitate was measured. The reduction in content of retinol palmitate was calculated; see Table 1.

Embodiment 1

18.0 g rice bran wax (percentage in total mass of the system: 3%, the same below) and 18.0 g (3%) tocopherol by weighing were provided, and they were added into 180.0 g (30%) soybean oil as heated to the temperature of 90° C. Rice bran wax and tocopherol were quickly agitated to make them thoroughly dissolved, and a super-molecular solution was prepared for use thereafter. 384.0 g (64%) retinol palmitate microcapsule prepared in Embodiment 1 was taken by weighing, and was placed into the heat exchange tank of the coater; 0° C. air was supplied to the tank bottom to make retinol palmitate microcapsule fully suspend in the tank. The aforesaid super-molecular solution was sprayed while heated to the surface of retinol palmitate microcapsule. It was continued to fluidize for 10 min for gelation after spray to form a gel protection film covered on the surface of microcapsule, and eventually obtained 532.0 g retinol palmitate powder. Initial content of retinol palmitate in the powder was measured. 500.0 g aforesaid powder was taken by weighing, and was packed into the aluminum foil bag for acceleration for 6 months under the temperature of 40° C.±2° C. and humidity of 75%±5%; the content of retinol palmitate was measured; reduction in content of retinol palmitate was calculated; see Table 1.

Retinol palmitate microcapsule as prepared in Comparative Example 1 was provided and retinol palmitate powder as prepared in Embodiment 1 by weighing was provided, and 500.0 g enriched nutritive flour was prepared as per the addition volume of 10.0 μg/g. Initial content of retinol palmitate in the enriched flour was measured; enriched nutritive flour was packed and sealed into the aluminum foil bag, and stored under the temperature of 40° C.±2° C. and relative humidity of 75%±5% for 6 months. The content of retinol palmitate was measured, Reduction in content of retinol palmitate in enriched nutritive flour was calculated; see Table 1.

TABLE 1

Reduction (/%) in Content of Retinol Palmitate Following Acceleration for 6 Months under the Temperature of 40° C. and Humidity of 75%

| | Microcapsule/powder | | Nutritive enriched flour | |
|---|---|---|---|---|
| | Comparative example 1 | Embodiment 1 | Comparative example 1 | Embodiment 1 |
| Retinol palmitate | 15.86 | 10.47 | 20.38 | 12.68 |

Comparative Example 2

696.9 g of modified starch was taken by weighing, and was thoroughly dissolved through being mixed in 1.5 L water that was pre-heated to the temperature of 80° C. for further use as a wall material solution. 126.2 g retinol palmitate crystal, 43.8 g vitamin D3 crystal, 233.3 g vitamin E acetate, 86.7 g vitamin K1 oil and 9.2 g tocopherol were weighed and they were dissolved in 369.0 g maize oil as heated to the temperature of 60° C. When it was still hot, it was added into aforesaid wall material solution to prepare emulsified solution through high-speed shearing. The aforesaid emulsified solution was made into 1109.5 g compound vitamin microcapsule containing retinol palmitate, vitamin D3, vitamin E acetate and vitamin K1. An initial content of vitamins in the microcapsule was checked. 500.0 g aforesaid microcapsule was taken by weighing, and packed into the aluminum foil bag for acceleration for 6 months under the temperature of 40° C.±2° C. and humidity of 75%±5%. The content of vitamins was measured. Reduction in content of vitamins was calculated; see Table 2.

Embodiment 2

3.0 g bee wax (0.5%) and 3.0 g tocopherol (0.5%) were provided by weighing, and they were added into 84.0 g maize oil (14%) that was pre-heated to the temperature of 70° C. Quick agitation was conducted to thoroughly dissolve the tocopherol and bee wax to prepare the super-molecular solution for use. 510.0 g compound vitamin microcapsule (85%) was provided as prepared in Comparative Example 2 by weighing, and was placed into the heat exchange tank of the coater. 20° C. air was supplied to the tank bottom to make the microcapsule fully suspend. The aforesaid super-molecular solution was sprayed while heated from the top to the bottom on the surface of the compound microcapsule. The aforesaid super-molecular solution was continued to be fluidized for 10 min for gelation to form a gel protection film covered on the surface of microcapsule, and eventually 547.3 g compound vitamin powder was obtained. The initial content of vitamins in the microcapsule was measured. 500.0 g aforesaid powder was provided by weighing, and was packed into the aluminum foil bag for acceleration for 6 months under the temperature of 40° C.±2° C. and humidity of 75%±5%. The content of vitamins was measured. The reduction in content of vitamins was calculated; see Table 2.

The compound vitamin microcapsule as prepared in Comparative Example 2 was provided and compound vitamin powder as prepared in Embodiment 2 was provided by weighing, and they were made into aqueous dispersion solution respectively. They were added to the water solution prepared with a common whole milk powder for uniform mixing to prepare 500.0 g enriched nutritive milk powder containing 6.0 µg/g vitamins through spray and drying. Initial content of vitamins were measured in the enriched milk powder. The enriched milk powder was packed and sealed into the aluminum foil bag for storage for 6 months under the temperature of 40° C.±2° C. and relative humidity of 75%±5%. The content of vitamins was measured, Reduction in content of vitamins in the enriched milk powder was calculated; see Table 2.

TABLE 2

Reduction/%) in Vitamin Content Following Acceleration for 6 Months under the Temperature of 40° C. and Humidity of 75%

|  | Microcapsule/powder | | Nutritive enriched flour | |
|---|---|---|---|---|
|  | Comparative example 2 | Embodiment 2 | Comparative example 2 | Embodiment 2 |
| Retinol palmitate | 13.65 | 9.94 | 22.03 | 11.02 |
| Vitamin D3 | 11.98 | 7.85 | 17.92 | 10.87 |
| Vitamin E acetate | 6.85 | 3.32 | 8.99 | 5.56 |
| Vitamin K1 | 10.23 | 6.37 | 15.99 | 9.24 |

Comparative Example 3

1104.7 g gelatin was provided by weighing, and was agitated to be dissolved into 2.0 L water preheated to the temperature of 80° C. and the solution was used as wall material solution for use thereafter. 27.4 g β-carotene crystal and 6.9 g BHT were provided, and were dissolved into 101.1 g maize oil that was heated to the temperature of 60° C. and was add into aforesaid wall material solution through high-speed shearing to prepare emulsified solution while still hot. 1054.5 g β-carotene microcapsule was prepared from aforesaid emulsified solution through spray and drying. Initial content of β-carotene in the microcapsule was measured. 500.0 g aforesaid microcapsule was provided by weighing, and was packed into the aluminum foil bag for acceleration for 6 months under the temperature of 40° C.±2° C. and humidity of 75%±5% before measurement of content of β-carotene. The reduction in content of β-carotene was calculated; see Table 3.

Embodiment 3

9.0 g γ-oryzanol (1.5%), 6.0 g β-sitosterol (1%) and 18.0 g BHT (3%) were provided by weighing, and they were added into 180.0 g salad oil (30%) that was heated to the temperature of 100° C. Quick agitation was proceeded to make BHT, γ-oryzanol and β-sitosterol fully dissolved, and the super-molecular solution was prepared for use. 387.0 g β-carotene microcapsule (64.5%) prepared in Comparative Example 3 was provided, and it was placed into the heat exchange tank of the coater. 30° C. air was supplied to the tank bottom to make β-carotene microcapsule fully suspend in the tank. The aforesaid super-molecular solution was sprayed while hot on the surface of β-carotene microcapsule. It was continued to be fluidized for 10 min for gelation after spray to form a gel protection film covered on the surface of the microcapsule, and eventually 552.9 g β-carotene powder was obtained. Initial content of β-carotene in the powder was measured. 500.0 g aforesaid powder was provided by weighing, and was pack in the aluminum foil bag for acceleration for 6 months under the temperature of 40° C.±2° C. and humidity of 75%±5% before measurement of content of β-carotene. Reduction in content of β-carotene was calculated; see Table 3.

TABLE 3

Reduction (/%) in Content of β-Carotene Following Acceleration for 6 Months under the Temperature of 40° C. and Humidity of 75%

|  | Comparative example 3 | Embodiment 3 |
|---|---|---|
| β-carotene | 6.86 | 3.47 |

Comparative Example 4

139.4 g lycopene crystal and 7.1 g TBHQ were provided by weighing, and were dissolved into 6 L dichloromethane to prepare lycopene solution. The aforesaid lycopene solution was added into the protective gel solution as formed by dissolving 1040.6 g modified starch into 2 L water. The addition was supplemented with high-speed shearing. The high-speed shearing was proceeded for 1 hour upon completion of addition, and then proceeded with depressurization to remove dichloromethane. After that, 995.9 g lycopene microcapsule was further prepared through spray and drying. The initial content of lycopene in the microcapsule was measured. 500.0 g aforesaid microcapsule was provided by weighing, and was packed into the aluminum foil bag for acceleration for 6 months under the temperature of 40° C.±2° C. and humidity of 75%±5% before measurement of content of lycopene. Reduction in content of lycopene was calculated; see Table 4.

Embodiment 4

18.0 g carnauba wax (3%) and 3.0 g TBHQ (0.5%) were taken by weighing, and were added into 87.0 g rap oil (14.5%) while heated to the temperature of 80° C. Quick agitation was proceeded to make TBHQ and carnauba wax full dissolved, and the super-molecular solution was prepared for use. 492.0 g (82%) lycopene microcapsule as prepared in Comparative Example 4 was provided by weighing, and was put into the heat exchange tank of the coater. 25° C. air was supplied to the tank bottom to make lycopene microcapsule fully suspend in the tank. The aforesaid super-molecular solution was sprayed while heated on the surface of the lycopene microcapsule, and continued to be fluidized for 10 minutes for gelation to form a gel protection film covered on the surface of the microcapsule, and eventually 546.9 g lycopene powder was obtained. Initial content of lycopene in the powder was measured. 500.0 g aforesaid powder was provided by weighing, and was packed in the aluminum foil bag for acceleration for 6 months under the temperature of 40° C.±2° C. and humidity of 75%±5% before measurement of content of lycopene. Reduction in content of lycopene was calculated; see Table 4.

500.0 g lycopene tablets were prepared as per formulation for health care product in Table 5 by taking lycopene as prepared in Comparative Example 4 and Embodiment 4 as material. All constituents were precisely taken for uniform mixing prior to tablet compressing. The initial content of lycopene in the table was measured. Lycopene was put and sealed the table into the special plastic bottle for storage for 6 months under the temperature of 40° C.±2° C. and relative humidity of 75%±5% before measurement of content of lycopene. Reduction in content of lycopene in the health care tablet was calculated; see Table 4.

TABLE 4

Reduction (/%) in Vitamin Content Following Acceleration for
6 Months under the Temperature of 40° C. and Humidity of 75%

| | Microcapsule/powder | | Tablet | |
|---|---|---|---|---|
| | Comparative example 4 | Embodiment 4 | Comparative example 4 | Embodiment 4 |
| Lycopene | 10.23 | 7.37 | 25.87 | 13.98 |

TABLE 5

Health Care Product Formulation

| Constituents | Mass/g |
|---|---|
| Lycopene | 1.1937 |
| β-carotene | 2.3900 |
| Retinol palmitate | 2.4049 |
| Ascorbic acid | 24.0400 |
| Vitmamin D3 | 2.4200 |
| Vitamin E | 11.5700 |
| Vitamin B1 | 1.1637 |
| Vitamin B2 | 0.7279 |
| Vitamin B6 | 1.4412 |
| Nicotinamide | 4.4600 |
| Folate | 1.1223 |
| Biotin | 0.7268 |
| D-calcium pantothenate | 3.9700 |
| Dibasic calcium phosphate | 260.53 |
| Magnesium oxide | 16.3400 |
| Zinc oxide | 6.1400 |
| Microcrystalline Cellulose | 40.0500 |
| CMS-Na | 11.9800 |
| Magnesium stearate | 40.0500 |
| Silicon dioxide | 2.8900 |
| Total | 399.5705 |

Comparative Example 5

114.5 g canthaxanthin crystal, 114.5 g lutein crystal and 7.1 g ethoxyquin were provided by weighing, and were dissolved into 12 L dichloromethane to prepare mixed solution of canthaxanthin and lutein. The aforesaid mixed solution of canthaxanthin and lutein were slowly added into the protective gel solution as formed by dissolving 921.0 g modified starch into 2 L water. The addition was supplemented with high-speed shearing. High-speed shearing was continued to be proceeded with for 1 hour after addition. After that, depressurization was proceeded with to remove dichloromethane, and 975.6 g canthaxanthin and lutin microcapsule were prepared through spray and drying. The initial content of canthaxanthin and lutin in the microcapsule were measured. 500.0 g aforesaid microcapsule by weighing was taken, and was packed into the aluminum foil bag for acceleration for 6 months under the temperature of 40° C.±2° C. and humidity of 75%±5%. The content of canthaxanthin and lutein were measured. The reduction in content of canthaxanthin and lutein was calculated; see Table 6.

Embodiment 5

18.0 g glycerin monostearate (3%) and 12.0 g ethoxyquin (2%) were provided by weighing, and were added into 144.0 g sunflower seed oil (24%) which was heated to the temperature of 100° C. Quick agitation was conducted to make ethoxyquin and glycerin monostearate fully dissolved, and the super-molecular solution was prepared for use. 426.0 g (71%) canthaxanthin and lutein were prepared, and was put into the heat exchange tank of the coater. 25° C. air was supplied to the tank bottom to make carotenoid microcapsule fully suspend. The aforesaid super-molecular solution was supplied while heated on the surface of carotenoid microcapsule, and proceed with fluidization for 10 minutes for gelation to form a gel protection film on the surface of the microcapsule, and eventually obtained 533.8 g carotenoid powder. Initial content of canthaxanthin and lutein in the powder was measured. 500.0 g aforesaid powder was provided by weighing, and was packed into the aluminum foil bag for acceleration for 6 months under the temperature of 40° C.±2° C. and humidity of 75%±5%. The content of canthaxanthin and lutein were measured. Reduction in content of canthaxanthin and lutein was calculated; see Table 6.

The carotenoid microcapsule as prepared in Comparative Example 5 and carotenoid powder as prepared in Embodiment 5 were provided by weighing, and 500.0 g premix was prepared as per premix formulation in Table 7. Initial content of canthaxanthin and lutein in the premix were measured. The premix was put and sealed into the aluminum foil bag for storage for 6 months under the temperature of 40° C.±2° C. and relative humidity of 75%±5% before measurement of content of canthaxanthin and lutein. Reduction in content of canthaxanthin and lutein in the premix was calculated; see Table 6.

TABLE 6

Reduction (%) in Content of Canthaxanthin and Lutein
Following Acceleration for 6 Months under the
Temperature of 40° C. and Humidity of 75%

| | Microcapsule/powder | | Premix | |
|---|---|---|---|---|
| | Comparative example 5 | Embodiment 5 | Comparative example 5 | Embodiment 5 |
| Canthaxanthin | 7.32 | 4.58 | 16.95 | 8.57 |
| Lutein | 8.38 | 5.94 | 18.63 | 10.41 |

TABLE 7

Premix Formulation

| Constituents | Mass/g |
|---|---|
| Canthaxanthin | 2.5060 |
| Lutein | 1.7080 |
| Astaxanthin | 0.8000 |
| Vitamin A acetate | 9.1800 |
| Vitamin D3 | 4.3000 |
| Vitamin E acetate | 19.0000 |
| Vitamin K3 | 0.7840 |
| Vitamin B1 nitrate | 0.4360 |
| Folate | 0.5000 |
| Niacinamide | 8.0400 |
| Calcium pantothenate | 3.3300 |
| Biotin | 2.0000 |
| Ethoxyquin | 0.0835 |
| Rice chaff | 47.3300 |
| Total | 100.0000 |

Comparative Example 6

151.9 g astaxanthin crystal and 10.9 g BHT were provided by weighing in reference to the method described in CN100421650C, and added into 6 L dichloromethane to prepare astaxanthin solution. After that, aforesaid solution was slowly added into the pot containing 60 L ethanol. A Millipore filter with bore diameter of 0.3 um was used for filtration after spray. The filter cake was washed and pressed with ethanol to obtain superfine filter cake of astaxanthin powder. The aforesaid filter cake of astaxanthin powder was mixed with 3 L aqueous solution containing 1110.4 g gelatin for agitation and beating prior to homogenizing in the high-pressure homogenizer for 4 hours. 1101.7 g astaxanthin microcapsule was prepared through spray and drying. Initial content of astaxanthin in the microcapsule was measured. 500.0 g aforesaid microcapsule was provided by weighing, and packed into the aluminum foil bag for acceleration for 6 months under the temperature of 40° C.±2° C. and humidity of 75%±5%; The content of astaxanthin was measured. The reduction in content of astaxanthin was calculated; see Table 8.

Embodiment 6

3.0 g candelilla wax (0.5%) and 3.0 g BHT (0.5%) were provided by weighing, and added into 36.0 g peanut oil (6.0%) which was heated to the temperature of 80° C. Quick agitation was conducted to make BHT and candelilla wax fully dissolved, and the super-molecular solution was prepared for use. 558.0 g (93%) astaxanthin microcapsule as prepared in Comparative Example 6 was provided by weighing, and was put into the heat exchange tank of the coater. 20° C. air was supplied to make the astaxanthin microcapsule fully suspend in the tank. The aforesaid super-molecular solution was sprayed while being heated on the surface of the astaxanthin microcapsule. After that, fluidization was conducted for 10 min for gelation to form a gel protection film covered on the surface of microcapsule, and eventually 548.7 g astaxanthin powder was obtained. Initial content of the astaxanthin in the powder was measured. 500.0 g aforesaid powder was taken and packed with an aluminum foil bag for acceleration under the temperature of 40° C.±2° C. and humidity of 75%±5% for 6 months before measurement of content of astaxanthin. Reduction in content of astaxanthin was calculated; see Table 8.

Astaxanthin microcapsule as prepared in Comparative Example 6 and astaxanthin powder as prepared in Embodiment 6 were provided by weighing, and a premix as per premix formulation in Table 7 was prepared. After that, the premix obtained was prepared into 500.0 g feedstuff as per feedstuff formulation as shown in Table 9. Initial content of astaxanthin in the feedstuff was measured, put and sealed into the aluminum foil bag for storage under the temperature of 40° C.±2° C. and humidity of 75%±5% for 6 months before measurement of content of astaxanthin. Reduction in content of astaxanthin was calculated; see Table 8.

TABLE 8

Reduction (/%) in Content of Astaxanthin Following Acceleration under the Temperature of 40° C. and Humidity of 75% for 6 Months

| | Microcapsule/powder | | Feedstuff | |
| --- | --- | --- | --- | --- |
| | Comparative example 6 | Embodiment 6 | Comparative example 6 | Embodiment 6 |
| Astaxanthin | 6.23 | 3.37 | 25.87 | 17.98 |

TABLE 9

Feedstuff Formulation

| Constituents | Maize | Bean Pulp | Rice bran | Bone meal | Choline chloride | Bluestone | Mineral | Premix |
| --- | --- | --- | --- | --- | --- | --- | --- | --- |
| Mass/g | 500 | 200 | 240 | 10 | 10 | 10 | 10 | 20 |

The invention claimed is:

1. A vitamin and carotenoid powder comprising a vitamin and carotenoid microcapsule and a physical gel protection film surrounding an outer surface of the vitamin and carotenoid microcapsule;
   wherein the vitamin and carotenoid microcapsule comprises the following compositions of parts by weight:
   vitamin and carotenoid as a core material of the microcapsule: 10.9-36.5 parts;
   antioxidant A: 0.1-1 part; and
   water soluble colloid as the outer surface of the microcapsule: supplemented to 100 parts;
   wherein the vitamin and carotenoid in the vitamin and carotenoid microcapsule are at least one of vitamin A palmitate, vitamin A acetate, vitamin D3, vitamin K1, β-carotene, astaxanthin, lycopene, canthaxanthin and lutein;
   wherein the antioxidant A is vitamin C, vitamin C sodium salt, iso-vitamin C or iso-vitamin C sodium salt; the water soluble colloid is starch octenyl succinate, or acacia;
   wherein the physical gel protection film is made from a super-molecular system; the super-molecular system consists of compositions of the following parts by weight:

| vegetable oil | 6~30 parts; |
| --- | --- |
| gel | 0.5~3 parts; and |
| antioxidant | 0.5~3 parts. | wherein the vegetable oil is at least one of rape oil, maize oil, sunflower seed oil, and peanut oil;
   wherein the gel is a mixture of γ-oryzanol and β-rhamno;
   wherein the antioxidant B is butylated hydroxytoluene (BHT) or tert-butylhydroquinone (TBHQ);
   wherein the physical gel protection film is formed by a process as follows:
   thoroughly suspending the vitamin and carotenoid microcapsule in a fluidizing air through ventilation; then spraying the super-molecular system on the outer surface of the vitamin and carotenoid microcapsule when the super-molecular system is hot to form the physical gel protection film;
   wherein the physical gel protection film is an inverted helical tubular structure formed by constituents of the super-molecular system through crystallization or self-assembly during cooling.

2. The vitamin and carotenoid powder according to claim 1, characterized in that the vegetable oil is maize oil, or sunflower seed oil.

3. The vitamin and carotenoid powder according to claim 1, characterized in that the antioxidant B is butylated hydroxytoluene (BHT).

4. The vitamin and carotenoid powder according to claim 1, wherein the compositions of the vitamin and carotenoid microcapsule in the powder is 64%-93% by weight.

5. The vitamin and carotenoid powder according to claim 1, characterized in that the vitamin and carotenoid microcapsule comprises the following compositions of parts by weight:
vitamin and carotenoid 36.5 parts;
antioxidant A 1 part; and
water soluble colloid supplemented to 100 parts.

6. The vitamin and carotenoid powder according to claim 1, wherein the antioxidant A is iso-vitamin C sodium salt; the water soluble colloid is starch octenyl succinate.

7. The vitamin and carotenoid powder according to claim 1, wherein the vitamin and carotenoid in the vitamin and carotenoid powder are at least one of vitamin A palmitate, vitamin A acetate, vitamin D3, and vitamin K1.

8. A vitamin and carotenoid powder comprising a vitamin and carotenoid microcapsule and a physical gel protection film surrounding an outer surface of the vitamin and carotenoid microcapsule;
wherein the vitamin and carotenoid microcapsule comprises the following compositions of parts by weight:
vitamin and carotenoid as a core material of the microcapsule: 10.9-36.5 parts;
antioxidant A: 0.1-1 part; and
water soluble colloid as the outer surface of the microcapsule: supplemented to 100 parts;
wherein the vitamin and carotenoid in the vitamin and carotenoid microcapsule are at least one of vitamin A palmitate, vitamin A acetate, vitamin D3, vitamin K1, β-carotene, astaxanthin, lycopene, canthaxanthin and lutein;
wherein the antioxidant A is vitamin C, vitamin C sodium salt, iso-vitamin C or iso-vitamin C sodium salt; the water soluble colloid is starch octenyl succinate, or acacia;
wherein the physical gel protection film is made from a super-molecular system; the super-molecular system consists of compositions of the following parts by weight:

| | |
|---|---|
| vitamin and carotenoid | 10.9-36.5 parts; |
| antioxidant A | 0.1-1 part; and |
| water soluble colloid | supplemented to 100 parts. | wherein the vegetable oil is at least one of rape oil, maize oil, sunflower seed oil, and peanut oil;
wherein the gel is a mixture of γ-oryzanol and β-rhamno;
wherein the antioxidant B is butylated hydroxytoluene (BHT) or tert-butylhydroquinone (TBHQ);
wherein the physical gel protection film is formed by a process as follows:
thoroughly suspending the vitamin and carotenoid microcapsule in a fluidizing air through ventilation; then spraying the super-molecular system on the outer surface of the vitamin and carotenoid microcapsule when the super-molecular system is hot to form the physical gel protection film;
wherein the physical gel protection film is an inverted helical tubular structure formed by constituents of the super-molecular system through crystallization or self-assembly during cooling;
wherein the physical gel protection film blocks gaps and pores on the outer surface of microcapsule to prevent contact and reaction between oxygen coming in from the gaps and pores on the outer surface of microcapsule, and prevents outward migration of the vitamin and carotenoid through the physical gel protection film, to achieve an improved stability of the vitamin and carotenoid such that, when the vitamin and carotenoid powder is sealed for storage under the temperature of 40° C±2° C. and humidity of 75%±5% for 6 months, and has a reduction rate.

9. The vitamin and carotenoid powder according to claim 8, wherein the vitamin and carotenoid in the vitamin and carotenoid microcapsule is retinol palmitate, and the reduction rate of retinol palmitate is about 10.47%.

10. The vitamin and carotenoid powder according to claim 8, wherein the vitamin and carotenoid in the vitamin and carotenoid microcapsule are vitamin D3 and vitamin K1, and wherein the reduction rate of vitamin D3 is about 7.85%, the reduction rate of vitamin K1 is about 6.37%.

11. The vitamin and carotenoid powder according to claim 8, wherein the vitamin and carotenoid in the vitamin and carotenoid microcapsule is β-carotene, and the reduction rate of β-carotene is about 3.47%.

12. The vitamin and carotenoid powder according to claim 8, wherein the vitamin and carotenoid in the vitamin and carotenoid microcapsule is lycopene, and the reduction rate of lycopene is about 7.37%.

13. The vitamin and carotenoid powder according to claim 8, wherein the vitamin and carotenoid in the vitamin and carotenoid microcapsule are canthaxanthin and lutein, the reduction rate of canthaxanthin is about 4.58% and the reduction rate of lutein is about 5.94%.

14. The vitamin and carotenoid powder according to claim 8, wherein the vitamin and carotenoid in the vitamin and carotenoid microcapsule is astaxanthin, and the reduction rate of astaxanthin is about 3.37%.

* * * * *